United States Patent [19]

Sattler et al.

[11] Patent Number: 5,980,970
[45] Date of Patent: Nov. 9, 1999

[54] LOTIONS CONTAINING FATTY ACID DERIVATIVES

[75] Inventors: Henning Sattler, Hamburg; Dagmar Zelle, Bliedersdorf, both of Germany

[73] Assignee: Beiersdorf AG, Hamburg, Germany

[21] Appl. No.: 08/860,919

[22] PCT Filed: Jan. 11, 1996

[86] PCT No.: PCT/EP96/00102

§ 371 Date: Sep. 25, 1997

§ 102(e) Date: Sep. 25, 1997

[87] PCT Pub. No.: WO96/22079

PCT Pub. Date: Jul. 25, 1996

[30] Foreign Application Priority Data

Jan. 18, 1995 [DE] Germany ............... 195 01 288

[51] Int. Cl.⁶ .................................................. A23D 7/00
[52] U.S. Cl. .................. 426/611; 426/601; 426/531; 426/583; 426/656; 426/688
[58] Field of Search ..................... 426/611, 601, 426/804, 531, 583, 656, 688

[56] References Cited

U.S. PATENT DOCUMENTS

| 3,658,555 | 4/1972 | Menz et al. ............... 99/122 R |
| 4,992,293 | 2/1991 | Klemann et al. ............... 426/11 |
| 5,093,142 | 3/1992 | Klemann et al. ............... 426/583 |
| 5,413,804 | 5/1995 | Rhodes ............... 426/531 |

FOREIGN PATENT DOCUMENTS 009216184  10/1992  WIPO .

*Primary Examiner*—Terressa Mosley
*Attorney, Agent, or Firm*—Sprung Kramer Schaefer & Briscoe

[57] ABSTRACT

The invention relates to W/O lotions having a content of at least one unsaturated fatty acid derivative, which are characterized in that they comprise W/O emulsifiers, W/O stabilizers and/or W/O emulsion systems chosen from the group consisting of (A) a W/O emulsifier based on ethoxylated castor oil,
(B) a W/O emulsifier (B1) based on sorbitan isostearate and a W/O stabilizer (B2) based on a polyalkylene glycol copolymer and
(C) a W/O emulsion system based on a methoxypolyalkylene glycol copolymer, either
  (1) the W/O emulsifier of (A) being used, or
  (2) the W/O emulsifier (B1) being used together with the W/O stabilizer B2 (B), or
  (3) a combination comprising emulsifiers (A) and (B) with (B1) and (B2) being used, where, in each case,
  (4) the emulsion system (C) can also be used together with (1) or (2) or (3), and water and, if appropriate, additives or auxiliaries.

6 Claims, No Drawings

LOTIONS CONTAINING FATTY ACID DERIVATIVES

The invention relates to lotions having a content of derivatives of unsaturated fatty acids.

Lotions offer the advantage over other topical formulations that they are easier to apply and to distribute, especially when used over large areas, and are absorbed into the skin better than creams or ointments. This applies in particular to lotions of the W/O type. From the type of emulsion, they are suitable for dry states of the skin. The bioavailability of incorporated substances is furthermore usually better than that from anhydrous topical formulations, and often also better than that from O/W lotions.

However, W/O lotions are difficult to stabilize. In the presence of relatively large proportions of esters of higher fatty acids, they tend to separate into the fatty phase and aqueous phase during storage.

Furthermore, if unsaturated fatty acid derivatives with one or more double bonds are employed in such lotions, there is a higher sensitivity to oxidation than when they are incorporated into anhydrous topical formulations.

W/O lotions having a high content of unsaturated fatty acids or derivatives thereof and good use properties which both are stable pharmaceutically and are also largely insensitive to oxidative influences during storage can be realized only with difficulty. This applies above all in the case of relatively high contents of these fatty acids or derivatives thereof.

Lotions in which the unsaturated fatty acids are subject to a relatively high oxidation effect are unsuitable for topical use. This is especially the case when used on already damaged and diseased skin, as is the case, for example, with atopy and psoriasis patients. Even with dry states of the skin, however, the oxidation decomposition products, such as peroxides, aldehydes and ketones, have an adverse effect and destroy the benefit of such preparations. The oxidative influence of sunlight manifests itself in particular.

The object of the invention was to provide water-in-oil lotions (W/O type) which are stable and in which at the same time the unsaturated fatty acids are not subject, or are subject to only a minor, non-troublesome extent, to harmful oxidative degradation.

The object of the invention has been achieved in that W/O emulsifiers and combinations with other emulsion constituents have been found which both stabilized the lotion in the presence of high proportions of unsaturated fatty acids or derivatives thereof and kept the unsaturated fatty acids stable to oxidation.

The invention relates to W/O lotions having a content of at least one unsaturated fatty acid derivative, which are characterized in that they comprise W/O emulsifiers, W/O stabilizers and/or W/O emulsion systems chosen from the group consisting of (A) a W/O emulsifier based on ethoxylated castor oil,
(B) a W/O emulsifier (B1) based on sorbitan isostearate and a W/O stabilizer (B2) based on a polyalkylene glycol copolymer and
(C) a W/O emulsion system based on a methoxy-polyalkylene glycol copolymer, either
  (1) the W/O emulsifier of (A) being used, or
  (2) the W/O emulsifier (B1) being used together with the W/O stabilizer B2 (B), or
  (3) a combination comprising emulsifiers (A) and (B) with (B1) and (B2) being used, where, in each case,
  (4) the emulsion system (C) can also be used together with (1) or (2) or (3), and water and, if appropriate, additives or auxiliaries.

The W/O emulsifier (A) used is preferably an ethoxylated hydrogenated castor oil which contains, in particular, seven ethylene oxide units. Such products are obtainable, for example, under the CTFA designation "PEG-7 hydrogenated castor oil" and under the trade name "Cremophor WO 7" (BASF, DE) or the name "Arlacel 989" (Atlas Chemie, ICI, DE).

W/O emulsifiers (B1) which are preferably used are polyethylene or polypropylene glycol-1 glycerol. sorbitan isostearates, or else products known under the CTFA-designation "sorbitan isostearate+PEG-2 hydrogenated castor oil+ozocerite+hydrogenated castor oil". A commercial product known under the-name "Arlacel 582" (Atlas Chemie, ICI, DE) is particularly suitable.

The preferred W/O stabilizer (B2) is a polyethylene glycol/dodecyl glycol copolymer having, in particular, 45 ethylene glycol units. Such stabilizers are also known under the CTFA designation "PEG-45/dodecyl glycol copolymer". A product marketed under the trade name "Elfacos ST 9" (Akzo Chemie GmbH, DE) is preferred.

The preferred W/O emulsion system (C) is a methoxy/polyethylene/dodecyl glycol copolymer, having, in particular, 22 ethylene glycol units. It is known under the CTFA designation "methoxy PEG-22/dodecyl glycol copolymer" and is obtainable as a commercial product under the name "Elfacos E 200" (Akzo Chemie GmbH, DE). W/O lotions according to the invention having a content of (C) are preferred.

The proportion of emulsifiers, stabilizers and emulsion systems can be 0.5 to 20% by weight, based on the total weight of the lotion.

If emulsifiers (A) or (B) are used individually, they are preferably employed in amounts of (A) of 3 to 12% by weight or of (B1) of 0.5 to 5 and (B2) of 0.2 to 5% by weight, in each case based on the total weight of the lotion.

Component (C), which is optionally added, for example, as an emulsion system, is then preferably present in amounts of from 0.1 to 5% by weight, also in each case based on the total weight of the lotion.

Preferably, the emulsifiers according to the invention are used together, and preferably also together with emulsion system (C), and in particular especially in the following amounts by weight, in each case based on the total weight of the formulations or lotions:

|      | % by weight |              | % by weight |
| ---- | ----------- | ------------ | ----------- |
| (A)  | 0.1–10,     | in particular | 0.5–5      |
| (B1) | 0.1–10,     | in particular | 0.5–5      |
| (B2) | 0.1–10,     | in particular | 0.2–5      |
| (C)  | 0.1–10      | in particular | 0.1–5      |

The lotions according to the invention can comprise one derivative or two or more derivatives of unsaturated fatty acids.

The fatty acid derivative according to the invention usually contains an unsaturated fatty acid. However, it can also contain two or more unsaturated fatty acids. Triglycerides can contain, for example, one, two or three unsaturated fatty acids.

Fatty acids, which are suitable according to the invention, of the fatty acid derivatives are mono- or polyunsaturated carboxylic acids having preferably 16–24 carbon atoms and, in particular, 1 to 6 double bonds, particularly preferably having one double bond or two or three double bonds.

The unsaturated fatty acids can belong both to the n-6 series and to the n-3 series. Fatty acids of the n-6 series are preferred.

Preferred derivatives of the fatty acids are the esters, for example the glycerides and, in particular, the triglycerides, or the esters with alcohols, in particular monoalkanols having preferably 1 to 5 carbon atoms, particularly preferably the ethyl esters.

The compounds can be employed both having been prepared synthetically and also in the naturally occurring form, for example as plant oils.

Derivatives which contain unsaturated carboxylic acids of chain length $C_{16}$–$C_{18}$ having one double bond, carboxylic acids of chain length $C_{16}$–$C_{20}$ having 2 double bonds, carboxylic acids of chain length $C_{18}$–$C_{20}$ having 3 double bonds and carboxylic acids of chain length $C_{20}$–$C_{22}$ having 5 or 6 double bonds are particularly preferred. The double bonds can be present both in isolated and also in conjugated form. Particularly preferred fatty acids having one double bond are oleic acid and palmitoleic acid. In the case of fatty acids having 2 double bonds, linoleic acid is particularly preferred; in the case of those having 3 double bonds alpha- and gamma-linolenic acid, dihomogamma-linolenic acid and arachidonic acid are particularly preferred; and in the case of those having or 6 double bonds eicosapentaenoic and docosahexaenoic acid are particularly preferred.

Particularly preferred esters are the triglycerides and the ethyl esters, in particular for the fatty acids mentioned by name.

The triglycerides can contain both 3 uniform, identical fatty acids and also one or 2 or 3 different fatty acids according to the invention, and they can contain both 3 uniform unsaturated fatty acids and also one or more different unsaturated fatty acids.

Particularly preferred compounds are the ethyl esters and triglycerides of linoleic acid, of alpha- and gamma-linolenic acid, of dihomogamma-linolenic acid and of eicosapentaenoic acid and dicosahexaenoic acid, but in particular of gamma-linolenic acid. The preferred oils which comprise the unsaturated fatty acids as triglycerides are olive oil, sunflower seed oil, evening primrose seed oil, borage oil, grapeseed oil, soybean oil, groundnut oil, wheatgerm oil, blackcurrant seed oil, the oil from specific fungi and fish oils.

The proportion of fatty acid derivatives according to the invention in the lotions can be, for example, 0.1 to 30% by weight, preferably 0.5 to 20% by weight, but in particular 1 to 5% by weight, in each case based on the total weight of the lotion.

The lotion according to the invention can also additionally comprise additives or auxiliaries.

The lotions according to the invention are distinguished by a low sensitivity to oxidation, so that additions of antioxidants are not absolutely necessary. If such additives are nevertheless desired, the amounts used can remain small.

Preferred antioxidants are butyl-hydroxy-toluene, butyl-hydroxy-anisole, tert-butyl-hydroxy-quinone, ascorbic acid and its derivatives, such as ascorbyl palmitate and Mg ascorbyl phosphate, tocopherols and their derivatives, such as alpha-tocopheryl acetate, gallates, such as propyl gallate, octyl gallate and dodecyl gallate, or other esters. The lotions can comprise antioxidants, for example, in amounts of 0.001 to 5% by weight, preferably 0.01 to 1% by weight. Other suitable antioxidants are t-butylhydroquinone, di-t-butylhydroquinone and di-alpha-tocopherol.

The lotions can furthermore comprise complexing agents, in particular in combination with the antioxidants, preferably EDTA, for example in amounts by weight of 0.01 to 5% by weight, in particular 0.1 to 1% by weight, based on the total lotion. Other suitable complexing agents are beta-alaninediacetic acid, hydroxyethylethylenediaminetriacetic acid ($Na_3HEDTA$), nitrilotriacetic acid or propylenediaminetetraacetic acid.

The lotions according to the invention can comprise fatty alcohols and mineral oils (paraffins).

Preferred fatty alcohols are myristyl alcohol, cetyl alcohol, stearyl alcohol, cetylstearyl alcohol, behenyl alcohol and 2-octyldodecanol (Eutanol G).

The paraffin used is preferably thinly liquid paraffin, if appropriate also in combination with semisolid (vaseline) or solid paraffin and microwaxes. Straight-chain and branched-chain paraffins are particularly preferred.

To establish the pH of, for example, pH 3–8, preferably pH 4 to pH 7, the lotion according to the invention can comprise acid additions and additions of salts thereof in small proportions of, for example, about 0.01–10% by weight, preferably 0.1 to 5% by weight, in each case based on the total weight of the lotion. Carboxylic acids, such as succinic acid, lactic acid, citric acid or else phosphoric acid, and salts thereof, are particularly suitable as buffers.

Preservatives and stabilizers can also be added. Substances such as parabens, benzalkonium chloride, p-chlorom-cresol, benzoic acid, sorbic acid, phenoxyethanol, benzyl alcohol, methyldibromoglutaric acid nitrile and mixtures thereof, for example, are suitable. The lotion can comprise them in amounts of 0.001–5% by weight, in particular 0.01 to 2% by weight.

The emulsifiers which are suitable for the W/O lotions are types of sometimes very complex compositions with low HLB values and mixtures thereof. The choice of emulsifiers has been made from the standpoint of achieving a W/O lotion which is stable for several years—even at elevated temperatures—and compatibility thereof with the active compounds and stabilization of the active compounds over the period mentioned.

The fatty phase of the W/O lotion comprises, for example, a balanced mixture of liquid, straight- or branched-chain paraffins, naturally occurring and synthetic esters of branched- or straight-chain, saturated fatty acids with mono- or polyhydric alcohols (for example isopropyl palmitate, myristate, stearate or isostearate, myristyl myristate, cetyl palmitate, medium-chain triglycerides and hydrogenated castor oil), and furthermore fatty acids (for example linoleic or linolenic acid and oleic acid), squalane and/or squalene, in amounts of, for example, in each case 0.1–30% by weight, preferably 0.5 to 10% by weight, in particular 1 to 5% by weight, based on the total lotion. The individual substances or mixtures can be used.

The lotions according to the invention can comprise further additives or auxiliaries.

The aqueous phase comprises, for example, polyhydric alcohols (for example glycerol, sorbitol, propylene glycol, 1,3-butylene glycol and polyethylene glycols), for example in amounts of in each case 1–10% by weight.

Unless stated otherwise, all the amounts data, contents and percentage contents are based on the weight.

A W/O lotion which is distinguished by a good activity, dermatological acceptance and high storage stability is provided by the new lotion according to the invention.

Compared with a W/O cream, the W/O lotion offers the great advantage that, in contrast to the former, in spite of the same type of emulsion, it can be distributed better, is absorbed faster into the skin and leaves behind no troublesome greasy film.

To prepare the lotion, the constituents of the fatty phase, such as paraffin and the emulsifier combination, are melted and brought to elevated temperature, for example 60° C., to 80° C., in a manner known per se. Glycerol and magnesium sulphate and constituents of the aqueous phase are dissolved in water at a higher temperature. The phases are combined and emulsified. The active compound is added at a lower temperature, for example 60°–80° C. The composition is allowed to cool, while stirring.

The active compound is absorbed very well from the lotion according to the invention, which has an outstanding storage stability. The lotion is used, for example, for the treatment of atopy (for example neurodermatitis), eczemas, dermatitis, psoriasis and inflammations, or in cosmetics.

To cure or treat these diseases, the lotion according to the invention can be applied topically to the damaged areas. The amount of lotion applied varies according to the concentration of the active compound. In general, a suitable amount is applied to the damaged area several times daily, depending on the severity of the disease to be treated.

Unless stated otherwise, all the amounts data, contents and percentage contents are based on the weight and the total amount or on the total weight of the formulations.

The following examples are intended to illustrate the present invention without limiting it.

The W/O lotion is prepared as follows. The constituents of the fatty phase, such as paraffin and emulsifier (combination), are heated to about 80° C. in a mixer-homogenizer which can be evacuated. The constituents of the aqueous phase, such as glycerol and magnesium sulphate and acids or buffer substances, are then dissolved in the water content at about 80° C.; the aqueous phase is added to the fatty phase in the mixer and the active compound is then added. A vacuum is applied and the mixture is cooled to about 25° C., while stirring and homogenizing. Preservatives are dissolved—depending on their physical and chemical properties—either in the fatty phase at about 80° C. or in the aqueous phase at about 80° C., or are added to the batch at about 40° C.

The following W/O emulsifiers, W/O stabilizers or W/O emulsion systems are used in the following examples.

(A) W/O emulsifier ethoxylated, hydrogenated castor oil with 7 ethylene oxide units (CTFA designation "PEG-7 hydrogenated castor oil")

(B1) W/O emulsifier with the CTFA designation "sorbitan isostearate+PEG-2 hydrogenated castor oil+ozocerite+hydrogenated castor oil"

(B2) W/O stabilizer polyethylene glycol/dodecyl glycol copolymer with 45 ethylene glycol units (CTFA designation "PEG-45/dodecyl glycol copolymer")

(C) W/O emulsion system methoxypolyethylene/dodecyl glycol copolymer with 22 ethylene glycol units (CTFA designation "methoxy PEG-22/dodecyl glycol copolymer")

EXAMPLE 1

A W/O lotion is prepared as stated above with the stated constituents:

|  | % by weight |
| --- | --- |
| Evening primrose oil | 22.2 |
| (C) Elfacos E 200 | 1 |
| (B1) Arlacel 582 | 2 |
| (B2) Elfacos ST 9 | 1 |
| (A) Cremophor WO 7 | 2 |
| Paraffin oil | 2.5 |
| Octyldodecanol (Eutanol G) | 5 |

-continued

|  | % by weight |
| --- | --- |
| Glycerol | 3 |
| Magnesium sulphate | 0.5 |
| Propyl gallate | 0.075 |
| Phenoxyethanol | 0.5 |
| Sodium benzoate | 0.2 |
| Benzoic acid | 0.1 |
| Water (distilled) | to 100 |

Example 1a

The procedure is as stated in Example 1, but instead of evening primrose oil, the same amount by weight of soybean oil is used.

Example 1b

The procedure is as stated in Example 1, but instead of evening primrose oil, the same amount by weight of sunflower seed oil is used.

Example 1c

The procedure is as stated in Example 1, but instead of evening primrose oil, the same amount by weight of groundnut oil is used.

Example 1d

The procedure is as stated in Example 1, but instead of evening primrose oil, the same amount by weight of wheatgerm oil is used.

Example 1e

The procedure is as stated in Example 1, but instead of evening primrose oil, the same amount by weight of grapeseed oil is used.

Example 1f

The procedure is as stated in Example 1, but instead of evening primrose oil, the same amount by weight of olive oil is used.

The preparation is carried out as stated above. The preservative phenoxyethanol is dissolved in the aqueous phase.

EXAMPLE 2

A W/O lotion is prepared as stated above with the stated constituents:

|  | % by weight |
| --- | --- |
| (A) Cremophor WO 7 | 7 |
| Paraffin oil | 9 |
| Cetearyl octanoate | 5 |
| Glycerol | 3 |
| Evening primrose oil | 11 |
| Magnesium sulphate | 0.7 |
| Propyl gallate | 0.05 |
| Benzyl alcohol | 1 |
| Water (distilled) | to 100 |

EXAMPLE 3

A W/O lotion is prepared as stated above with the stated constituents:

|  | % by weight |
|---|---|
| Evening primrose oil | 22.2 |
| (C) Elfacos E 200 | 0.075 |
| (B1) Arlacel 582 | 1.5 |
| (B2) Elfacos ST 9 | 0.75 |
| (A) Arlacel 989 | 1.5 |
| Paraffin oil | 2.5 |
| Octyldodecanol | 4.5 |
| Glycerol | 3 |
| Magnesium sulphate | 0.5 |
| Propyl gallate | 0.075 |
| Phenoxyethanol | 0.5 |
| Sodium benzoate | 0.2 |
| Benzoic acid | 0.1 |
| Water (distilled) | to 100 |

EXAMPLE 4

A W/O lotion is prepared as stated above with the stated constituents:

|  | % by weight |
|---|---|
| Evening primrose oil | 22.2 |
| (C) Elfacos E 200 | 1 |
| (B1) Arlacel 582 | 4 |
| (B2) Elfacos ST 9 | 1.5 |
| Paraffin oil | 2.5 |
| Octyldodecanol | 4.5 |
| Glycerol | 3 |
| Magnesium sulphate | 0.5 |
| Propyl gallate | 0.075 |
| Phenoxyethanol | 0.5 |
| Sodium benzoate | 0.2 |
| Benzoic acid | 0.1 |
| Water (distilled) | to 100 |

EXAMPLE 5

|  | % by weight |
|---|---|
| Gamma-linolenic acid ethyl ester | 3 |
| (C) Elfacos E 200 | 0.75 |
| (B1) Arlacel 582 | 1.5 |
| (B2) Elfacos ST 9 | 0.75 |
| (A) Cremophor WO 7 | 1.5 |
| Paraffin oil | 12.5 |
| Octyldodecanol | 5 |
| Glycerol | 3 |
| Magnesium sulphate | 0.5 |
| Ascorbyl palmitate | 0.01 |
| Disodium EDTA | 0.1 |
| Benzyl alcohol | 1.5 |
| Perfume | 0.1 |

EXAMPLE 6

A W/O lotion is prepared as stated above with the stated constituents:

|  | % by weight |
|---|---|
| Linoleic acid ethyl ester | 5 |
| (C) Elfacos E 200 | 1 |
| (B1) Arlacel 582 | 2 |
| (B2) Elfacos ST 9 | 1 |
| (A) Cremophor WO 7 | 2 |
| Paraffin oil | 2.5 |
| Caprylic acid/capric acid triglyceride | 4.5 |
| Glycerol | 3 |
| Magnesium sulphate | 0.5 |
| Propyl gallate | 0.075 |
| Phenoxyethanol | 0.5 |
| p-Hydroxybenzoic acid ethyl ester | 0.7 |
| Water (distilled) | to 100 |

EXAMPLE 7

A W/O lotion is prepared as stated above with the stated constituents:

|  | % by weight |
|---|---|
| Borage oil | 10.0 |
| (B1) Arlacel 582 | 2 |
| (B2) Elfacos ST 9 | 2 |
| (A) Cremophor WO 7 | 2 |
| Paraffin oil | 10 |
| Octyldodecanol | 4.5 |
| Glycerol | 5 |
| Magnesium sulphate | 0.5 |
| Tocopherol acetate | 0.5 |
| Phenoxyethanol | 0.5 |
| Sodium benzoate | 0.2 |
| Benzoic acid | 0.1 |
| Water (distilled) | to 100 |

EXAMPLE 8

A W/O lotion is prepared as stated above with the stated constituents:

|  | % by weight |
|---|---|
| (A) Arlacel 989 | 7 |
| Paraffin oil | 9 |
| Octyldodecanol | 5 |
| Sorbitol | 3 |
| Blackcurrant seed oil | 10 |
| Magnesium sulphate | 0.7 |
| BHT | 0.1 |
| Benzyl alcohol | 1 |
| Water (distilled) | to 100 |

EXAMPLE 9

A W/O lotion is prepared as stated above with the stated constituents:

|  | % by weight |
|---|---|
| Grapeseed oil | 15 |
| Elfacos E 200 | 1 |
| (A) Cremophor WO 7 | 5 |
| Paraffin oil | 2.5 |
| Octyldodecanol | 4.5 |
| Propylene glycol | 5 |
| Magnesium sulphate | 0.5 |

-continued

|  | % by weight |
| --- | --- |
| Propyl gallate | 0.075 |
| Phenoxyethanol | 0.5 |
| Na sorbate | 0.2 |
| Sorbic acid | 0.1 |
| Water (distilled) | to 100 |

We claim:

1. W/O lotions having a content of at least one unsaturated fatty acid derivative, which comprise W/O emulsifiers, W/O stabilizers and/or W/O emulsion systems selected from the group consisting of
    (A) a W/O emulsifier based on ethoxylated castor oil,
    (B) a W/O emulsifier (B1) based on sorbitan isostearate and a W/O stabilizer (B2) based on a polyalkylene glycol copolymer and
    (C) a W/O emulsion system based on a methoxy-polyalkylene glycol copolymer, either
        (1) the W/O emulsifier of (A) being used, or
        (2) the W/O emulsifier (B1) being used together with the W/O stabilizer B2 (B), or
        (3) a combination comprising emulsifiers (A) and (B) with (B1) and (B2) being used, where, in each case,
        (4) the emulsion system (C) can also be used together with (1) or (2) or (3), and water and, if appropriate, additives or auxiliaries.

2. W/O lotions according to claim 1, wherein the lotions comprise emulsion system (C).

3. W/O lotions according to claim 1, wherein the fatty acids of the fatty acid derivatives are mono- or polyunsaturated carboxylic acids having 16–24 carbon atoms.

4. W/O lotion according to claim 1, wherein the fatty acid is gamma-linolenic acid.

5. W/O lotion according to claim 1, wherein the derivatives are triglycerides or esters.

6. W/O lotion according to claim 1, wherein the lotion comprises antioxidant and/or a complexing agent.

* * * * *